United States Patent
Elliott et al.

(10) Patent No.: US 6,699,846 B2
(45) Date of Patent: *Mar. 2, 2004

(54) MONO- AND DISACCHARIDES FOR THE TREATMENT OF NITRIC OXIDE RELATED DISORDERS

(75) Inventors: Gary T. Elliott, Stevensville, MT (US); David Johnson, Hamilton, MT (US); Patricia Weber, Stevensville, MT (US); Greg Sowell, Bothell, WA (US)

(73) Assignee: Corixa Corporation, Seattle, WA (US)

(*) Notice: Subject to any disclaimer, the term of this patent is extended or adjusted under 35 U.S.C. 154(b) by 59 days.

This patent is subject to a terminal disclaimer.

(21) Appl. No.: 09/808,669

(22) Filed: Mar. 14, 2001

(65) Prior Publication Data

US 2002/0045586 A1 Apr. 18, 2002

Related U.S. Application Data

(60) Provisional application No. 60/190,444, filed on Mar. 17, 2000.

(51) Int. Cl.[7] .................. A61K 31/715; C08B 37/00
(52) U.S. Cl. .................. 514/53; 514/54; 514/175; 536/53; 536/55; 536/55.1; 536/123.13
(58) Field of Search .................. 514/53, 54, 175; 536/53, 55, 55.1, 123.13

(56) References Cited

U.S. PATENT DOCUMENTS

| | | |
|---|---|---|
| 4,436,727 A | 3/1984 | Rib |
| 4,912,094 A | 3/1990 | Myers et al. |
| 4,912,094 A | 2/1994 | Myers et al. |
| 5,286,718 A * | 2/1994 | Elliott .................. 514/54 |
| 6,013,640 A * | 1/2000 | Elliott et al. .................. 514/53 |
| 6,113,918 A * | 9/2000 | Johnson et al. .......... 424/278.1 |
| 6,303,347 B1 * | 10/2001 | Johnson et al. .............. 435/101 |
| 6,355,257 B1 | 3/2002 | Johnson et al. |

FOREIGN PATENT DOCUMENTS

| | | |
|---|---|---|
| WO | WO 93/12778 A1 | 7/1993 |
| WO | WO 98/50399 A1 | 11/1998 |
| WO | WO 00/11010 A1 | 3/2000 |

OTHER PUBLICATIONS

Johnson, D.A. et al. "Synthesis and Biological Evaluation of a New Class of Vaccine Adjuvants: Aminoalkyl Glucosaminide 4–Phosphates (AGPs)," *Bioorganic & Medicinal Chemistry Letters* 1999, pp. 2273–2278, vol. 9.

Johnson, D.A. et al. "3–O–Desacyl Monophosphoryl Lipid A Derivatives: Synthesis and Immunostimulant Activities," *J. Med. Chem.* 1999, pp. 4640–4649, vol. 42.

Xi, L. et al. "Glycolipid RC–552 Induces Delayed Preconditioning–Like Effect Via iNOS–Dependent Pathway in Mice," *Am. J. Physiol.* 1999, pp. h2418–h2424, vol. 277, No. 6.

* cited by examiner

*Primary Examiner*—Samuel Barts
*Assistant Examiner*—Devesh Khare
(74) *Attorney, Agent, or Firm*—Townsend and Townsend and Crew LLP

(57) ABSTRACT

Methods for treating diseases or conditions modulated or ameliorated by nitric oxide, particularly ischemia and reperfusion injury, are provided, using glycolipids structurally related to monophosphoryl lipid A but with notable reduction in proinflammatory and pyrogenic activity.

35 Claims, 1 Drawing Sheet

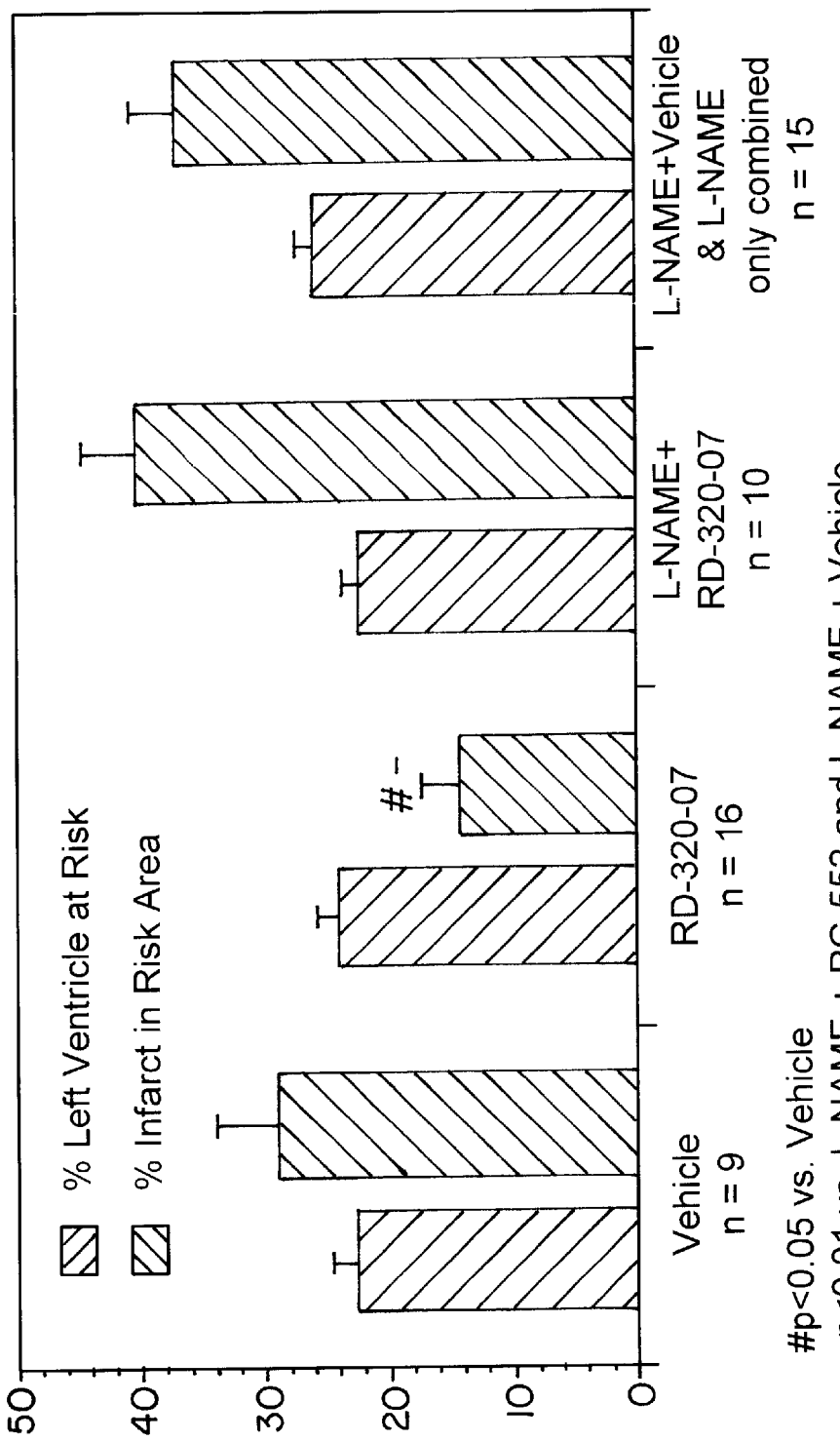

US 6,699,846 B2

MONO- AND DISACCHARIDES FOR THE TREATMENT OF NITRIC OXIDE RELATED DISORDERS

CROSS-REFERENCES TO RELATED APPLICATIONS

This application claims priority to U.S. Provisional Patent Application Serial No. 60/190,444, filed on Mar. 17, 2000. This application is related to application Ser. No. 09/429,238, filed Oct. 28, 1999 which is a continuation of application Ser. No. 09/138,305, filed Aug. 21, 1998, now U.S. Pat. No. 6,013,640; application Ser. No. 07/815,250, filed Dec. 31, 1991, now U.S. Pat. No. 5,286,718, and application Ser. No. 09/439,839, filed Nov. 12, 1999 which is a continuation-in-part of application Ser. No. 08/853,826, filed May 8, 1997. Each of the above-referenced disclosures is incorporated herein by reference in its entirety for all purposes.

STATEMENT AS TO RIGHTS TO INVENTIONS MADE UNDER FEDERALLY SPONSORED RESEARCH AND DEVELOPMENT

Not applicable

BACKGROUND OF THE INVENTION

Damage caused to tissues during ischemia/reperfusion can be extensive. Tissues deprived of oxygen suffer both reversible and irreversible damage. Injured tissues can also display disorders in automaticity. For example, myocardial tissues damaged during ischemia/reperfusion can display irreversible damage or myocardial infarction. Reversible damage, or stunning, is apparent with reduced pump efficiency leading to decreased cardiac output and symptomatology of suboptimal organ perfusion. Reperfusion of ischemic myocardial tissue may also cause electrophysiologic changes causing disorders in automaticity, including lethal arrhythmias.

The exact mechanisms by which tissues are damaged during ischemia/reperfusion are unknown. It is hypothesized, however, that a complex series of events occur where tissues are damaged during ischemia as well as during subsequent reperfusion. During ischemia, tissues are deprived of oxygen-giving blood leading to anaerobic metabolism and consequently intracellular acidosis. Lack of circulation can cause infarcts or areas of necrotic, dead tissue. Ischemic tissues produce less of the enzymes needed to scavenge free radicals. Upon reperfusion and re-exposure to oxygen, tissues are damaged when free radicals including hydroxyl radicals are produced. Oxidative damage also disrupts the calcium balance in surrounding tissues causing stunning. Damage due to the oxidative burst is further compounded when injured cells release factors which draw inflammatory neutrophils to the ischemic site. The inflammatory cells produce enzymes which produce more toxic free-radicals and infiltrate the interstitial spaces where they kill myocytes.

Methods to protect against the damage due to ischemia/reperfusion injury focus on reducing anaerobic metabolism as well as the initial oxidative burst and ensuing calcium overload preventing subsequent inflammation-associated damage. For example, agents which either decrease the production of oxygen-derived free radicals (including allopurinol and deferoxamine) or increase the catabolism of these materials such as superoxide dismutase, catalase, glutathione, and copper complexes, appear to limit infarct size and also may enhance recovery of left ventricular function from cardiac stunning. Agents which block sarcolemmal sodium/hydrogen exchange such as amiloride prevent the obligatory influx of calcium into the cell attendant with sodium extrusion and consequently reduce calcium overload.

Tissues can also be protected from ischemia/reperfusion injury by ischemic preconditioning. Ischemic preconditioning is triggered by brief antecedent ischemia followed by reperfusion which results in the rapid development of ischemic tolerance. This acute preconditioned state of ischemic tolerance lasts 30 min to 2 h and in myocardial tissue is characterized by reduced infarct size and a reduced incidence of ventricular arrhythmias but not reduced levels of stunning (Elliott, *J. Mol. Cell Cardiol.*, 30(1):3–17 (1998)). Following dissipation of the acute preconditioned state, even in the absence of additional periods of preconditioning ischemia, a delayed preconditioned state of ischemic tolerance appears 12–24 h later and lasts up to 72 h. During the delayed phase of preconditioning protection against myocardial infarction, stunning and arrhythmia have been reported in various species.

Features of preconditioned myocardium in the face of ischemia/reperfusion include preservation of adenosine triphosphate (ATP) in some models, attenuation of intracellular acidosis and the reduction of intramyocyte calcium loading. Certain chemical agents known to be released by myocardium during ischemia have been shown to induce acute and delayed ischemic tolerance and provide cardiac protection. For example, adenosine, bradykinin and opiate receptor agonists which induce acute preconditioning and appear to protect from ischemic injury via ATP dependent potassium ($K_{ATP}$) channel signaling pathways. The agent, bimakalim, known to open the $K_{ATP}$ channel has also been shown to limit infarct size (Mizumura et al., *Circulation*, 92:1236–1245 (1995)). Monophosphoryl lipid A (MLA) prevents irreversible as well as reversible damage to ischemic tissues (Elliot U.S. Pat. No. 5,286,718). Monophosphoryl lipid A is a detoxified derivative of lipid A, the active substructural element of lipopolysaccharide (LPS). LPS or endotoxin is a potent immunomodulator produced by most strains of Gram-negative bacteria. Pretreatment with LPS prior to ischemia has been shown to increase myocardial catalase activity increasing myocardial function (Brown et al., *Proc. Natl. Acad. Sci. U.S.A*, 86(7):2516–2520 (1989), Bensard et al., *J. Surg. Res.*, 49(2):126–131 (1990)). Endotoxin also protects against lung injury during hypoxia (Berg et al., *J Appl. Physiol.*, 68(2):549–553 (1990), Berg et al., *Soc. Exper. Biol. Med.*, 167–170 (1990)). The cardioprotective effect of high doses of endotoxin appears to be associated with the ability of this "toxin" to induce upon pretreatment myocardial oxidative stress, thereby protecting from a second oxidative stress associated with ischemia (Maulik et al., *Am. J. Physiol.*, 269:C907–C916 (1995)). LPS however is quite toxic. MLA has been structurally modified to negate the toxicity of LPS. It is hypothesized that MLA protects against injury due to ischemia/reperfusion injury by inducing the production of nitric oxide synthase which leads to an enhanced open-state probability of the cardioprotective ATP-dependent potassium channel ($K_{ATP}$). The nitric oxide burst caused by MLA may also lead to a decrease in the number of inflammatory neutrophils entering the post-ischemic area protecting the patient from further injury. In contrast to endotoxin, MLA does not appear to induce myocardial oxidative stress at cardioprotective doses.

Current treatments for ischemia/reperfusion injury are not however without drawbacks. Many of the agents known to be active, do not have broad clinical applicability, have limited effectiveness, and/or have dose limiting toxicities and consequently have been restricted in their application to ameliorate ischemia/reperfusion injury in the heart. Endotoxin is highly toxic to the system at cardioprotective doses. MLA, while non-toxic, is manufactured by the fermentation of *S. minnesota* and, as is the case with many biological products, exists as a composite or mixture of a number of molecular congeners varying in fatty acid substitution patterns with varying fatty acid chain lengths.

Although in comparison with endotoxin, MLA is non-toxic at cardioprotective doses, MLA can cause mild, transient, although not dose-limiting, fever and flu-like symptoms in the target dose range. It should therefore be apparent from the above that a need remains for new compositions which are safe, effective and which have a broad clinical applicability in preventing or ameliorating the harmful effects of ischemia/reperfusion. Compositions which are non-toxic, non-pyrogenic, produced by chemical synthesis and of a single defined molecular structure would prove advantageous for this application. More specifically, there is a need for compounds which induce or activate nitric oxide signalling in a tissue-selective or specific fashion, wherein the compound upregulates nitric oxide (NO) in target tissues without inducing proinflammatory cytokines or NO at the level of the macrophage/monocyte and without pyrogenic effects. Surprisingly, the present invention provides such compounds.

SUMMARY OF THE INVENTION

In one aspect, the present invention provides methods for treating diseases or conditions mediated by nitric oxide, particularly ischemia and reperfusion injury. The methods comprise administering to a subject in need of such treatment an effective amount of a compound having the formula:

(I)

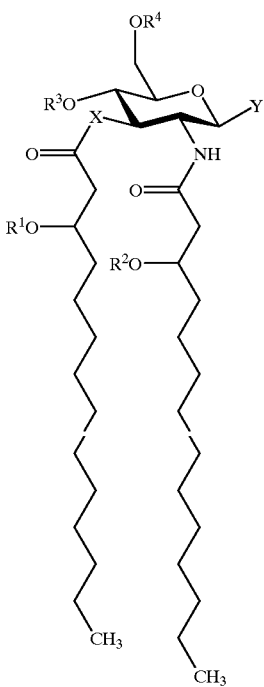

and pharmaceutically acceptable salts thereof, wherein X is —O— or —NH—; $R^1$ and $R^2$ are each independently a $(C_2-C_{24})$acyl group, including saturated, unsaturated and branched acyl groups; $R^3$ is —H or —$PO_3R^{11}R^{12}$, wherein $R^{11}$ and $R^{12}$ are each independently —H or $(C_1-C_4)$alkyl; $R^4$ is —H, —$CH_3$ or —$PO_3R^{13}R^{14}$, wherein $R^{13}$ and $R^{14}$ are each independently selected from —H and $(C_1-C_4)$alkyl; and Y is a radical selected from the formulae:

(Ia)

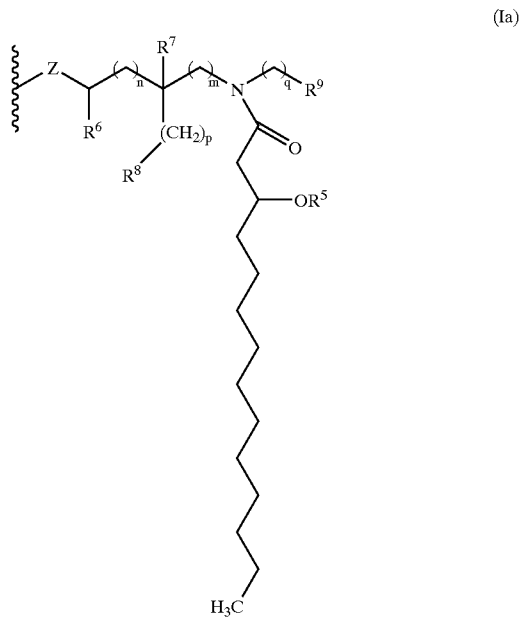

and (Ib)

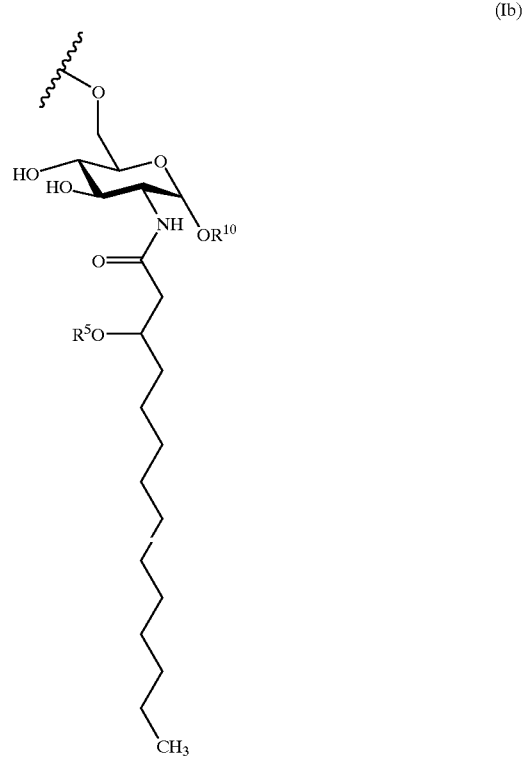

wherein the subscripts n, m, p and q are each independently an integer of from 0 to 6; $R^5$ is a $(C_2-C_{24})$acyl group (including, as above, saturated, unsaturated and branched acyl groups); $R^6$ and $R^7$ are independently selected from H and $CH_3$; $R^8$ and $R^9$ are independently selected from H, OH, $(C_1-C_4)$alkoxy, $-PO_3H_2$, $-OPO_3H_2$, $-SO_3H$, $-OSO_3H$, $-NR^{15}R^{16}$, $-SR^{15}$, $-CN$, $-NO_2$, $-CHO$, $-CO_2R^{15}$, and $-CONR^{15}R^{16}$, wherein $R^{15}$ and $R^{16}$ are each independently selected from H and $(C_1-C_4)$alayl; $R^{10}$ is selected from H, $CH_3$, $-PO_3H_2$, ω-phosphonooxy$(C_2-C_{24})$alkyl, and ω-carboxy$(C_1-C_{24})$alkyl; and Z is $-O-$ or $-S-$; with the proviso that when $R^3$ is $-PO_3R^{11}R^{12}$, $R^4$ is other than $-PO_3R^{13}R^{14}$.

The present invention also provides compounds which can be used in the present methods, as well as pharmaceutical compositions containing compounds of the general formula above.

BRIEF DESCRIPTION OF THE DRAWINGS

FIG. 1 is a graph illustrating the reduction in infarct size achieved with RC-552 in a pig model system.

DETAILED DESCRIPTION OF THE INVENTION AND THE PREFERRED EMBODIMENTS

Definitions:

The term "alkyl," by itself or as part of another substituent, means, unless otherwise stated, a straight or branched chain, or cyclic hydrocarbon radical, or combination thereof, which may be fully saturated, mono- or poly-unsaturated and can include di- and multivalent radicals, having the number of carbon atoms designated (i.e. $C_1-C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Typically, an alkyl group will have from 1 to 24 carbon atoms. A "lower alkyl" or is a shorter chain alkyl group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "acyl" refers to a group derived from an organic acid by removal of the hydroxy group. Examples of acyl groups include acetyl, propionyl, dodecanoyl, tetradecanoyl, isobutyryl, and the like. Accordingly, the term "acyl" is meant to include a group otherwise defined as $-C(O)$-alkyl.

Each of the above terms (e.g., "alkyl" "acyl") are meant to include both substituted and unsubstituted forms of the indicated radical. Preferred substituents for each type of radical are provided below.

Substituents for the alkyl and acyl radicals can be a variety of groups selected from: $-OR'$, $=O$, $=NR'$, $=N-OR'$, $-NR'R"$, $-SR'$, -halogen, $-SiR'R"R'''$, $-OC(O)R'$, $-C(O)R'$, $-CO_2R'$, $-CONR'R"$, $-OC(O)NR'R"$, $-NR"C(O)R'$, $-NR'-C(O)NR"R'''$, $-NR"C(O)_2R'$, $-NH-C(NH_2)=NH$, $-NR'C(NH_2)=NH$, $-NHC(NH_2)=NR'$, $-S(O)R'$, $-S(O)_2R'$, $-S(O)_2NR'R"$, $-CN$ and $-NO_2$ in a number ranging from zero to (2m'+1), where m' is the total number of carbon atoms in such radical. R', R" and R''' each independently refer to hydrogen and unsubstituted $(C_1-C_8)$alkyl. When R' and R" are attached to the same nitrogen atom, they can be combined with the nitrogen atom to form a 5-, 6-, or 7-membered ring. For example, $-NR'R"$ is meant to include 1-pyrrolidinyl and 4-morpholinyl. From the above discussion of substituents, one of skill in the art will understand that the term "alkyl" is meant to include groups such as haloalkyl (e.g., $-CF_3$ and $-CH_2CF_3$) and the like.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science*, 1977, 66, 1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

General

It is generally agreed that inducers of iNOS gene transcription and protein synthesis are proinflammatory and consequently somewhat "toxic" or poorly tolerated in animals and humans. Endotoxin (LPS) and proinflammatory cytokines such as IL-1, TNF and IFN-γ are known inducers of iNOS. All are inherently toxic and capable of inducing a systemic inflammatory response, adult respiratory distress syndrome, multiple organ failure and cardiovascular collapse when administered to animals.

Monophosphoryl lipid A is a structural derivative of lipid A (or LPS) and has an improved therapeutic index relative to lipid A. The compound can be safely administered to humans as doses up to at least 20 μg/kg, although increases in temperature, flu-like symptoms, increasing heart rate and modest decreases in blood pressure can occur in some patients at dose levels of ≧10 μg/kg. Cell culture and animal evaluations confirm that monophosphoryl lipid A (commercially sold as MPL® immunostimulant) still retains some of the immunostimulatory activity of the parent LPS in that pyrogenicity and the ability to induce pro-inflammatory cytokines such as TNF and IL-8 remain, albeit at higher dose levels.

Investigation of the cardioprotective activity of MPL® demonstrated that induction of nitric oxide synthases (iNOS) is important in the delayed cardioprotective effect of the compound. Additionally, nitric oxide (NO) signaling, presumably through constitutive pools of NOS, is important in the acute cardioprotective effect of the compound. In view of the residual endotoxic-like activity of MPL®, it is not surprising that the compound could be capable of inducing nitric oxide signaling. Still further, nitric oxide signaling has been suggested as a potential pathway by which ischemic preconditioning elicits cardioprotection. This observation in combination with the fact that nitric oxide donors are cardioprotective provides further support for the NOS/NO pathway as the route for MPL® cardioprotection.

In contrast, another glycolipid, RC-552, exhibits cardioprotective activity without appreciable endotoxic activity. For example, RC-552 does not induce fever in rabbits at doses of up to 1000 μg/kg in the same formulation in which MPL® causes fevers at about 10–15 μg/kg. Additionally, RC-552 does not elicit TNF, IL-1 or IL-8 from the human myelo-monocytic cell line THP-1 at concentrations up to 10,000 μg/mL in contrast with both MPL® and LPS. Evaluation of MPL® and RC-552 in a four hour exposure followed by approximately 20 hr drug-free incubation of monocytic cells to elicit nitrite elaboration (a measure of iNOS induction), from the murine macrophage cell line J774 indicates that MPL® is active with an $ED_{50}$ of about 40–80 ng/mL, while RC-552 is essentially inactive with a nominal $ED_{50}$ of about 720–1200 ng/mL.

Accordingly, RC-552 is without significant immunostimulatory (residual endotoxic) activity and does not induce iNOS in a monocytic cell line. Thus, RC-552 exhibits a unique profile in comparison with MPL® and various other synthetic mono- and disaccharides in that it is devoid of immunostimulatory activity and devoid of iNOS inductive potency in monocytic/macrophage cells such as J774, yet it is cardioprotective by a nitric oxide dependent pathway.

Other investigators have also found that the preconditioning effect achieved with RC-552 is due to an increase in nitric oxide levels produced through induction of an inducible form of nitric oxide synthase (iNOS). See, Xi, et al., Am. J. Physiol. 277(6 Pt 2):H2418–H2424 (1999).

These observations suggest a tissue selectivity or specificity for RC-552 not apparent with MPL or LPS.

The present invention provides other glycolipid compounds and compositions which have similar properties (low pyrogenicity and cytokine inductive activity), and which are useful in treating ischemia and reperfusion injury or other disease states or conditions which are modified by nitric oxide, such as conditions involving the regulation of vascular tone (e.g., vasospasm, pulmonary hypertension, systemic hypertension, impotence, alopecia and congestive heart failure), conditions arising from thrombotic (antiplatelet) events (e.g., transient ischemic attacks, intermittent claudication, myocardial infarction or stroke associated with acute thrombosis). Additionally, nitric oxide inducers can be useful as an adjunct to thrombolysis to improve thrombolytic effect and reduce acute reclosure and protect tissue in the event of reclosure due to preconditioning effects, restenosis after PTCA or stenting, and to prevent thrombosis leading to MI or stroke. Other conditions that can be treated with compounds described herein are in the field of obstetrics (e.g., to prevent or reverse pre-eclampsia and eclampsia and to stop premature labor); coronary and peripheral artery disease (e.g, to reduce arteriosclerosis and vasospasm (above)), pulmonary (e.g., adult respiratory distress syndrome (ARDS), chronic obstructive pulmonary disease (COPD), bronchospasm (asthma), prevention of septic shock and multiple organ failure as well as hypoxemia associated with thoracic surgery. Finally, certain compounds described herein will find use in cellular preservation (e.g., inhibit apoptosis, reduce ischemia/reperfusion injury in any organ as associated with transplantation, myocardial infarction, surgery, stroke and thrombosis, Alzheimer's and ischemic dementia).

While certain compounds within the present invention have been described as adjuvants and immunoeffectors (see WO 98/50399), no correlation between this activity and the compounds' ability to induce nitric oxide production in cells or tissues other than monocytes/macrophages has been previously described.

Compounds and Compositions

In one aspect, the present invention provides compounds having the formula:

(I)

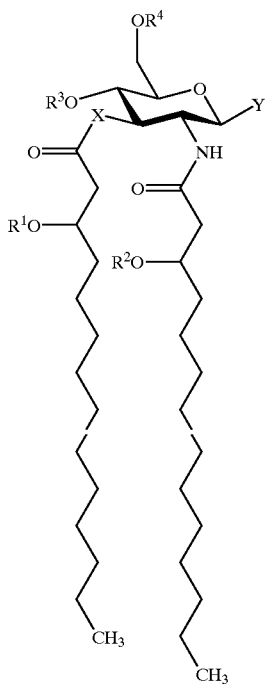

and pharmaceutically acceptable salts thereof, wherein X is —O— or —NH—; $R^1$ and $R^2$ are each independently a ($C_2$–$C_{24}$)acyl group, including saturated, unsaturated and branched acyl groups; $R^3$ is —H or —$PO_3R^{11}R^{12}$, wherein $R^{11}$ and $R^{12}$ are each independently —H or ($C_1$–$C_4$)alkyl; $R^4$ is —H, —$CH_3$ or —$PO_3R^{13}R^{14}$, wherein $R^{13}$ and $R^{14}$ are each independently selected from —H and ($C_1$–$C_4$)alkyl; and Y is a radical selected from the formulae:

(Ia)

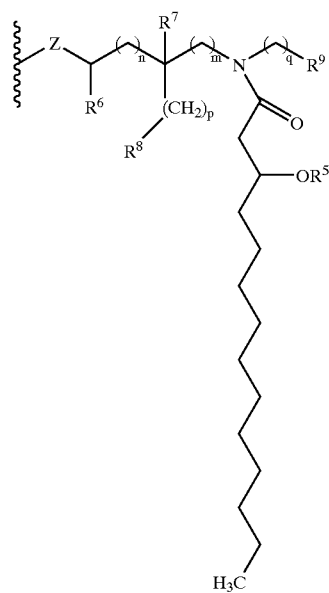

and (Ib)

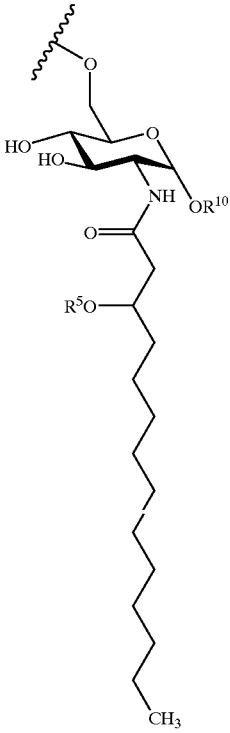

wherein the subscripts n, m, p and q are each independently an integer of from 0 to 6; $R^5$ is a ($C_2$–$C_{24}$)acyl group (including, as above, saturated, unsaturated and branched acyl groups); $R^6$ and $R^7$ are independently selected from H and $CH_3$; $R^8$ and $R^9$ are independently selected from H, OH, ($C_1$–$C_4$)alkoxy, —$PO_3H_2$, —$OPO_3H_2$, —$SO_3H$, —$OSO_3H$, —$NR^{15}R^{16}$, —$SR^{15}$, —CN, —$NO_2$, —CHO, —$CO_2R^{15}$, and —$CONR^{15}R^{16}$, wherein $R^{15}$ and $R^{16}$ are each independently selected from H and ($C_1$–$C_4$)alkyl; $R^{10}$ is selected from H, $CH_3$, —$PO_3H_2$, ω-phosphonooxy($C_2$–$C_{24}$)alkyl, and ω-carboxy($C_1$–$C_{24}$)alkyl; and Z is —O— or —S—; with the proviso that when $R^3$ is —$PO_3R^{11}R^{12}$, $R^4$ is other than —$PO_3R^{13}R^{14}$.

Additionally, when $R^3$ is —$PO_3H_2$, $R^4$ is H, $R^{10}$ is H, $R^1$ is n-tetradecanoyl, $R^2$ is n-octadecanoyl and $R^5$ is n-hexadecanoyl, then X is other than —O—.

In the general formula above, the configuration of the 3' stereogenic centers to which the normal fatty acid acyl residues are attached is R or S, but preferably R. The stereochemistry of the carbon atoms to which $R^6$ and $R^7$ are attached can be R or S. All stereoisomers, enantiomers, diastereomers and mixtures thereof are considered to be within the scope of the present invention.

In one group of preferred embodiments, Y has the formula:

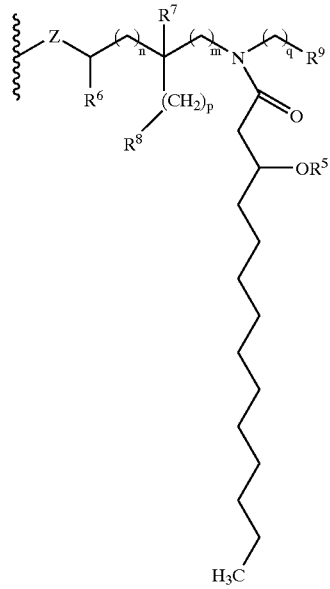

(Ia).

Within this group of embodiments, the acyl groups $R^1$, $R^2$ and $R^5$ will be selected such that at least two of the groups are ($C_2$–$C_6$)acyl. Further preferred are those embodiments in which the total number of carbon atoms in $R^1$, $R^2$ and $R^5$ is from about 6 to about 22, more preferably about from about 12 to about 18. In other preferred embodiments, X is O and Z is O. The subscripts n, m, p and q are preferably integers of from 0 to 3, more preferably, 0 to 2. Of the remaining substituents, $R^6$ and $R^7$ are preferably H. The present invention further contemplates those embodiments in which the preferred substituents are combined in one molecule.

In another group of embodiments, $R^1$, $R^2$ and $R^5$ are selected from ($C_{12}$–$C_{20}$)acyl with the proviso that the total number of carbon atoms in $R^1$, $R^2$ and $R^5$ is from about 44 to about 60. More preferably, the total number of carbon atoms in $R^1$, $R^2$ and $R^5$ is from about 46 to about 52. Still further preferred are those embodiments in which X and Z are both —O—.

In another group of preferred embodiments, Y has the formula:

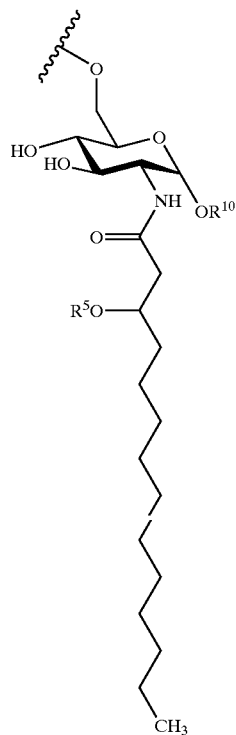

(Ib).

As with the group of preferred embodiments provided above, in this group the acyl groups $R^1$, $R^2$ and $R^5$ will also be selected such that at least two of the groups are ($C_2$–$C_6$) acyl. Further preferred are those embodiments in which the total number of carbon atoms in $R^1$, $R^2$ and $R^5$ is from about 6 to about 22, more preferably about from about 12 to about 18. In other preferred embodiments, X is O. Of the remaining substituents, $R^3$ is preferably phosphono (—$PO_3H_2$) and $R^4$ is preferably H. The present invention further contemplates those embodiments in which various combinations of the preferred substituents are combined in one molecule.

In another group of embodiments, $R^1$, $R^2$ and $R^5$ are selected from ($C_{12}$–$C_{24}$)acyl with the proviso that the total number of carbon atoms in $R^1$, $R^2$ and $R^5$ is from about 44 to about 60. More preferably, the total number of carbon atoms in $R^1$, $R^2$ and $R^5$ is from about 46 to about 52. Particularly preferred fatty acid groups for $R^1$, $R^2$ and $R^5$ are normal $C_{14}$, $C_{16}$ and $C_{18}$ fatty acid groups. Still further preferred are those embodiments in which X is —O—. Similar to the shorter acyl chain embodiments provided above, $R^3$ is preferably phosphono (—$PO_3H_2$) and $R^4$ is preferably H.

In the most preferred embodiments of the present invention, Y is a radical of formula (Ib), X is O, $R^3$ is phosphono, $R^4$ is H, and $R^1$, $R^2$ and $R^5$ are selected from ($C_{12}$–$C_{24}$)acyl with the proviso that the total number of carbon atoms in $R^1$, $R^2$ and $R^5$ is from about 46 to about 52. Still further preferred are those compounds in which $R^2$ is ($C_{16}$–$C_{18}$)acyl.

Preparation of Compounds

Certain compounds useful in the present invention are described in co-pending applications Ser. Nos. 08/853,826, 09/439,839 (filed Nov. 12, 1999) and in PCT/US98/09385. Other compounds can be prepared in a manner similar to that described for RC-552 (L34) in U.S. Pat. No. 6,013,640. Still other compounds can be prepared using methods outlined in Johnson, et al., *J. Med. Chem.* 42:4640–4649 (1999), Johnson, et al., *Bioorg. Med. Chem. Lett.* 9:2273–2278 (1999), and PCT/US98/50399. In general, the synthetic methods described in the above-noted references are broadly applicable to the preparation of compounds having different acyl groups and substitutions. One of skill in the art will appreciate that the convergent methods described therein can be modified to use alternate acylating agents, or can be initiated with commercially available materials having appropriate acyl groups attached.

Evaluation of Compounds

The compounds provided herein can be evaluated in a variety of assay formats to select a compound having a suitable pharmacophoric profile. For example, U.S. Pat. No. 6,013,640 describes animal models suitable for evaluating cardioprotective effects of compounds described herein. The examples below also provide assays for evaluating pyrogenicity of the subject compounds, and further assays for evaluating the proinflammatory effects of the compounds.

The present invention further provides pharmaceutical compositions comprising the compounds provided herein in admixture with one or more pharmaceutically acceptable carriers. Suitable carriers will depend on the condition being treated along with the route of administration. Accordingly, a discussion of the carriers is provided below in conjunction with the methods of use.

Methods of Use

The phosphoglycolipids of the subject invention are useful in ameliorating damage to metabolically active tissues such as, but not restricted to, heart tissue due to ischemia/reperfusion injury. Tissues are initially damaged during ischemia when they are deprived of oxygen. Oxygen deprivation during ischemia causes cell necrosis. Oxygen deprivation also leads to increased free-radical production upon reperfusion, activation of the complement pathway, upregulation of vascular adhesion molecules and the production of inflammatory cytokines. The compounds provided herein protect tissues deprived of oxygen during ischemia. It should be apparent to those skilled in the art that the subject compounds can also protect tissues experiencing all types of hypoxia or anoxia followed by reoxygenation.

It has been suggested that additional damage and cell death occurs upon the reintroduction of oxygen to the tissues by reperfusion. Free-radicals produced during reperfusion promote cell death. Free-radical damage to cells results in calcium overload and a decrease in activity of a variety of enzyme systems including, presumably, nitric oxide synthase causing a decrease in nitric oxide production leading to increases in neutrophil adhesion. The cardioprotective effect of the compounds of the subject invention can be blocked by aminoguanidine, a selective inhibitor of inducible nitric oxide synthase (iNOS) or L-NAME, a nonselective inhibitor of constitutive and inducible NOS isoforms. Administration of the drug blocked the delayed cardioprotective effect of RC-552 in dogs suggesting a nitric oxide-linked mechanism of action for the subject compound. Experiments conducted in iNOS knockout mice and the analogous wild strain mice confirm the role for iNOS induction and NO signaling in the delayed cardioprotective activity of RC-552.

Neutrophils are instrumental in the damaging inflammatory response which occurs in post-ischemic tissues. Neutrophils are called to the ischemic site by C5a and 5b (complement fragments), cytokines and chemokines which are chemotactic for the cell. Activated neutrophils attach to endothelial cells and diapedes across the endothelial barrier where they kill myocytes. Attachment and diapedesis of inflammatory neutrophils across the endothelial barrier are dependent upon the upregulation of adhesion molecules on both the endothelial surface and the neutrophil. Cytokines such as IL-6 produced by ischemic tissues have been shown to be crucial to the upregulation of adhesion molecules. The preferred compounds of the subject invention are unique in that at protective levels they do not induce pro-inflammatory cytokines (well-recognized inducers of NOS and NO synthesis) or fever yet are effective in ameliorating damage due to ischemia/reperfusion injury via an NO dependent mechanism.

In the clinical situation, ischemic events occur which are anticipated or unexpected. Planned surgeries causing ischemic events include coronary artery bypass surgery, heart valve replacement, cardiac angioplasty, ventricular septal repairs, surgery with major vessel cross-clamping, plastic surgery, skin flap translocation, myoplasty, organ or tissue transplant, aortic aneurysm repair or bowel resection. Tissues can be deprived of oxygen during unplanned events such as myocardial infarction, stroke, drowning, bowel infarct and traumatic amputation and reattachment. Unexpectedly, the phosphoglycolipid compounds of the subject invention provide both acute protection as well as delayed protection to ischemic tissues. Further, duration of the acute protective effect can be extended by infusion of the drug following a bolus dose.

The compounds provided herein exhibit a protective effect to ischemic tissues within minutes of administration of the compound to a patient. For example, administration of a compound of the subject invention to test animals 10 min before cardiac ischemia can induce protection shown by reduced infarct size arrythmias and stunning in treated animals. This immediate or acute protective effect dissipates or wanes in time. A delayed protective effect however becomes apparent approximately 24 h after administration of the drug. Delayed protection was evident in dogs and rabbits when animals were treated with, for example, RC-552 about 24 h before cardiac ischemia as illustrated by reduced infarct size and stunning. Protection provided by this compound to ischemic tissues is biphasic offering two distinct periods of protection, an acute period of protection and a delayed period of protection. It has been found that the acute protective effect of RC-552 (L34) can be extended for at least 3 h by infusion of the drug immediately following bolus dosing allowing a clinician to bridge the gap between acute and delayed periods of protection. The compounds provided herein are also advantageous in that they can be used successfully in emergency and trauma situations where it is not possible to dose well in advance of an oxygen depriving event. Further, the delayed protective effect provided by the compounds make the drug useful in situations where the ischemic events may occur even a day following administration of a single dose.

In methods for protecting against ischemic damage, the compounds provided herein can be formulated with a pharmaceutically acceptable carrier for injection, inhalation or intranasal, rectal or vaginal instillation or ingestion. As used herein, "pharmaceutically acceptable carrier" means a medium which does not interfere with the biological activity of the active ingredient and is not toxic to the patient to whom it is administered. Pharmaceutically acceptable carriers include oil-in-water or water-in-oil emulsions, aqueous compositions with or without inclusion of organic co-solvents suitable for intravenous (IV) use, liposomes or surfactant containing vesicles, microbeads and microsomes, powders, tablets, capsules, suppositories or aqueous suspensions and aerosols.

Formulations of the present compounds that can be administered parenterally, i.e. intraperitoneally, subcutaneously, intramuscularly or intravenously include the following preferred carriers. An example of a preferred carrier for intravenous use includes a mixture of 10% USP ethanol, 40% USP propylene glycol or polyethylene glycol 600 and the balance USP Water for Injection (WFI). Other acceptable carriers include 10% USP ethanol and USP WFI; 0.01–0.1% triethanolamine in USP WFI; or 0.01–0.2% dipalmitoyl diphosphatidylcholine in USP WFI; and 1–10% squalene or parenteral vegetable oil-in-water emulsion. Pharmaceutically acceptable parenteral solvents are such as to provide a solution or dispersion which may be filtered through a 0.22 micron filter without removing the active ingredient.

Examples of preferred carriers for subcutaneous or intramuscular use include phosphate buffered saline (PBS) solution, 5% dextrose in WFI and 0.01–0.1% triethanolamine in 5% dextrose or 0.9% sodium chloride in USP WFI, or a 1 to 2 or 1 to 4 mixture of 10% USP ethanol, 40% propylene glycol and the balance an acceptable isotonic solution such as 5% dextrose or 0.9% sodium chloride; or 0.01–0.2% dipalmitoyl diphosphatidylcholine in USP WFI and 1 to 10% squalene or parenteral vegetable oil-in-water emulsions.

Examples of carriers for administration via mucosal surfaces depend upon the particular route. When administered orally, examples include pharmaceutical grades of mannitol, starch, lactose, magnesium stearate, sodium saccharide, cellulose, magnesium carbonate and the like, with mannitol being preferred. When administered intranasally, polyethylene glycol, phospholipids, glycols and glycolipids, sucrose, and/or methylcellulose, powder suspensions with or without bulking agents such as lactose and preservatives such as benzalkonium chloride, EDTA, may be used. In a particularly preferred embodiment, the phospholipid 1,2 dipalmitoyl-sn-glycero-3-phosphocholine (DPPC) is a suitable isotonic aqueous carrier at 0.01–0.2% for intranasal administration of the compound of the subject invention at a concentration of 0.1 to 3.0 mg/ml. When administered by inhalation, suitable carriers are polyethylene glycol or glycols, DPPC, methylcellulose, powdered dispersing agents, and preservatives, with polyethylene glycols and DPPC being preferred.

The compounds of the subject invention can be administered to an individual in "an effective amount" to ameliorate or protect from ischemia/reperfusion injury. As used herein, "an effective amount" is that amount which shows a response over and above the vehicle or negative controls. The precise dosage of the compound of the subject invention to be administered to a patient will depend the route of administration, the pharmaceutical composition, and the patient. For example, when administered intravenously, to pigs to reduce infarct size after left anterior descending artery occlusion, the amount of compound used is from 1 to about 1000 micrograms/kg, preferably from about 10 to about 300 micrograms/kg, and most preferably from about 35 to about 100 micrograms per kilogram of body weight. Similarly, effective amounts suitable for the treatment of other conditions mediated, at least in part, by nitric oxide levels can be determined by the clinician according to standard protocols.

EXAMPLES

In the examples below, the effects of RC-552 on myocardial infarction, proinflammatory cytokine elaboration, pyrogenicity and iNOS induction (in myelomonocytic cells) are demonstrated. Other compounds provided herein exhibit similar profiles (exemplary data provided below).

Example 1

This example illustrates the effects which can be achieved using the compounds described herein. The example uses RC-552 in a pig infarct study.

The role of nitric oxide was evaluated by the administration of Nω-nitro-L-arginine methyl ester (L-NAME, a nonspecific inhibitor of nitric oxide synthase) prior to RC-552 dosing (in an ethanol/propylene glycol formulation). Initial experiments involved determination of an optimal dose of L-NAME, specifically a dose that would not alter hemodynamics or interfere with or aggravate the development of infarction but would potentially block the cardioprotective effect of RC-552. A dose of 0.5 mg/kg L-NAME, administered 30 minutes prior to dosing with RC-552 or vehicle (40 minutes prior to LAD occlusion) was found to be optimal.

Pigs were assigned in a randomized blinded fashion to one of five groups: 1) 0.5 mg/kg L-NAME administered 40 minutes prior to LAD occlusion; 2) 0.5 mg/kg L-NAME administered 30 minutes prior to a 29 $\mu$g/kg bolus, i.v. dose of RC-552; 3) 0.5 mg/kg L-NAME administered 30 minutes prior to a bolus dose of vehicle at a comparable weight adjusted volume (38.8 $\mu$L/kg); 4) 29 $\mu$g/kg bolus dose of RC-552 administered 10 minutes prior to LAD occlusion; and 5) a bolus dose of vehicle (38.8 $\mu$L/kg) administered 10 minutes prior to LAD occlusion. A total of 35 pigs were enrolled in the study: 8 in group 1; 10 in group 2; 7 in group 3, 7 in group 4; and 3 in group 5. When the data were analyzed, infarct size results from the two L-NAME control groups (1 and 3) were combined. In addition, infarct size results from pigs in a preceding study that were treated with RC-552 or vehicle 10 minutes before occlusion were added to groups 4 and 5, respectively.

As shown in FIG. 1, infarct size was reduced by 50% from a mean of 28.9±5.0% in vehicle pretreated pigs to 14.2±3.0% in pigs treated with RC-552 10 minutes prior to ischemia. Administration of L-NAME 30 minutes prior to RC-552 resulted in a mean infarct size of 40.2±4.4% vs. 36.9±3.7% for the combined group of L-NAME alone and L-NAME+vehicle. No significant differences were noted among the groups treated with vehicle only, L-NAME+RC-552 and L-NAME+vehicle. The results implicate a role for nitric oxide synthase in the acute cardioprotective effect induced by RC-552.

Example 2

This example illustrates the effects of various glycolipids on proinflammatory cytokine elaboration from the human myelomonocytic THP-1 cell line.

Methods:

The human myelomonocytic cell line THP-1 (ATCC) was used to evaluate the ability of glycolipids to induce proinflammatory cytokines. Glycolipids were added to cell suspensions of THP-1 as aqueous solutions containing 10% ethanol in water for injection. Prior to the 4 hr inductions, THP-1 cells are pre-incubated overnight with $10^{-7}$ M vitamin D3, washed three times and replated in the presence of MPL®, LPS or the synthetic compounds. After 4 hr coincubating of cells with glycolipids, media containing drug is removed, cells resuspended in fresh media and allowed to rest for 20 hr.

Results:

RC-552 was incapable of inducing secretion of the pyrogenic/proinflammatory cytokine TNF, even at a tissue culture concentration of 10,000 $\mu$g/mL in contrast with the positive control LPS which was an effective stimulator of TNF secretion from THP-1 cells at 1 ng/mL. MPL® was effective at inducing TNF in the concentration range of 100 to 10,000 ng/mL.

Evaluation of IL-8 elaboration revealed a similar trend to that observed with LPS being a potent inducer of IL-8 elaboration at 1 to 10 ng/mL and MPL® promoting cytokine release at 100 to 10,000 ng/mL. RC-552 was incapable of stimulating IL-8 secretion above background even at concentrations of 10,000 ng/mL.

Secretion of IL-1B was induced by LPS at 1 to 10 ng/mL, but was not induced by RC-552 at up to 10,000 ng/mL.

Example 3

This example illustrates the effects of RC-552 on body temperature in rabbits, dogs and rats.

In clinical trials with monophosphoryl lipid A, fever was generally the first observed side effect. In clinical studies of various formulations of monophosphoryl lipid A administered intravenously, moderate fever, flu-like symptoms and alterations in blood pressure seem to be side effects that establish maximally tolerated doses. Minimum pyrogenic monophosphoryl lipid A doses, adjusted for body weight, as determined in the USP rabbit pyrogen test agree well with results observed in humans. Evaluation of pyrogenicity of one formulation of RC-552 (10% ethanol in USP WFI) conducted in the three rabbit USP rabbit pyrogen test indicates the product is nonpyrogenic at intravenous doses up to at least 1,000 μg/kg (less than 0.35° C. average temperature increase). In contrast, monophosphoryl lipid A becomes pyrogenic at intravenous doses of approximately 15 μg/kg (temperature increase of about 0.5° C.). Similar studies with RC-552 in rats and dogs showed no detectable increase in temperatures at intravenous doses of up to 3000 μg/kg.

Example 4

This example illustrates the effects of various glycolipids on iNOS induction in J774 murine macrophages.

Methods:

The murine macrophage cell line J774 can be primed by IFN-γ in vitro and is very responsive to subsequent LPS stimulation of iNOS upregulation as measured by a standard Greiss reagent ELISA assay procedure. The assay utilizes J774 cells seeded at $1\times10^6$/mL with 30 mL/flask and with IFN-γ added at 100 units/mL for 16–24 hrs. Cells are then harvested and washed and resuspended at $2\times10^5$/well in a 96-well plate and allowed to adhere. Glycolipid compounds are serially diluted into the wells for a test group and the resulting cultures are incubated for another 36–40 hrs before culture supernatants are collected from Greiss reagent analysis of nitrite release. Nitrite content closely parallels iNOS function.

Results:

RC-552 and MPL® were first evaluated. Potency was determined as the concentration (ng/mL) of glycolipid in culture capable of inducing one-half maximal induction of nitrite ($ED_{50}$). The lower the $ED_{50}$ number, the greater the potency for iNOS induction.

MPL® was found to have an $ED_{50}$ of about 62 ng/mL resulting in high levels of nitrite elaboration while RC-552 exhibited a nominal $ED_{50}$ of about 977 ng/mL, with very low maximal iNOS activity observed, suggesting RC-552 was essentially inactive in this system for iNOS induction. These results further suggest that RC-552 may be cell or tissue specific in its ability to promote NO biosynthesis considering the dissimilar results for NOS activation in the J774 macrophage cell line versus cardiac protection models.

Example 5

This example illustrates the activities of compounds provided herein which exhibit a profile similar to that of RC-552. In the Table below, activity is expressed as follows: iNOS ($ED_{50}$)++<80; +, from 80–200; ->200; pyrogenicity (2.5 μg dose), ++>2° C.; +, from 1–2° C.; -<1° C.; cytokine induction (TNF-α, IL-1β) ++, observable @ 1 μg/mL; +, not detected @ 1 μg/mL but observable @ 10 μg/mL; -, not observable at 10 μg/mL.

Structures of the compounds are provided below the Table. Stereochemistry is provided for the centers to which $R^1O$—, $R^2O$— and $R^5O$— are attached, respectively.

TABLE

| Compound | iNOS ($ED_{50}$) | pyrogenicity | cytokine induction |
|---|---|---|---|
| 5.18 | − | + | − |
| 5.20 | − | − | ++ |
| 5.21 | − | − | − |
| 5.23 | − | − | − |
| 5.25 | + | − | ++ |
| 5.29 | − | − | ++ |
| 5.31 | − | − | − |
| 5.32 | − | ++ | − |
| RC-552 | − | − | − |

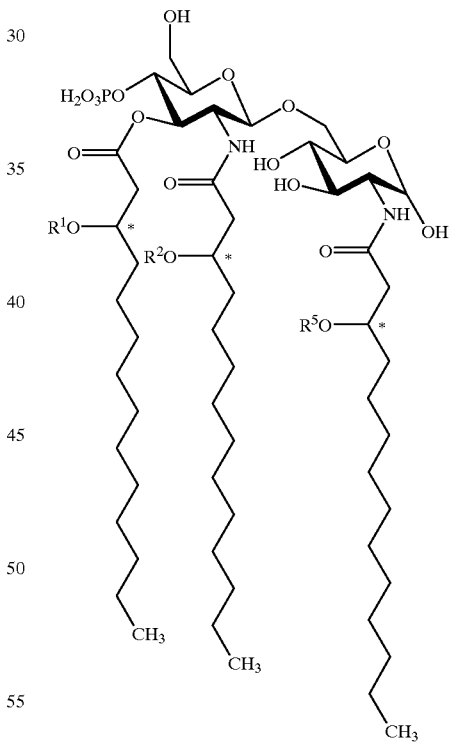

5.18: $R^1$ = acetyl; $R^2$ = acetyl; $R^5$ = acetyl (stereochemistry * R, R, R).

5.20: $R^1$ = tetradecanoyl; $R^2$ = tetradecanoyl; $R^5$ = hexadecanoyl (stereochemistry* R, R, R).

5.31: $R^1$ = hexanoyl; $R^2$ = hexanoyl; $R^5$ = hexanoyl (stereochemistry* R, R, R).

5.32: $R^1$ = butyryl; $R^2$ = butyryl; $R^5$ = butyryl (stereochemistry* R, R, R).

RC-552: $R^1$ = tetradecanoyl; $R^2$ = octadecanoyl; $R^5$ = hexadecanoyl (stereochemistry* R, R, R).

TABLE-continued

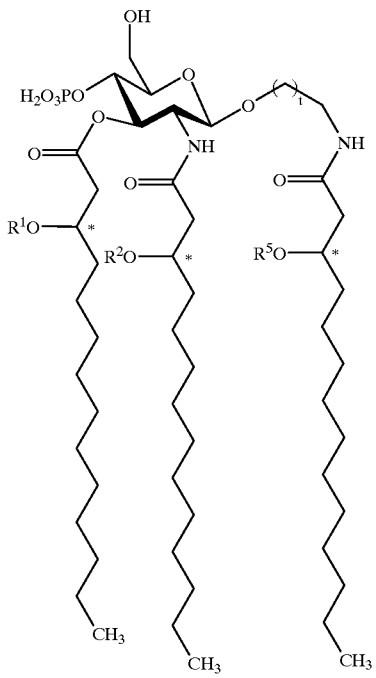

5.23: t = 1; $R^1$, $R^2$ and $R^5$ = hexanoyl (stereochemistry* R, R, R)
5.25: t = 2; $R^1$, $R^2$ and $R^5$ = tetradecanoyl (stereochemistry* R, R, R)
5.29: t = 1; $R^1$, $R^2$ and $R^5$ = tetradecanoyl (stereochemistry* R, R, R)
5.21:

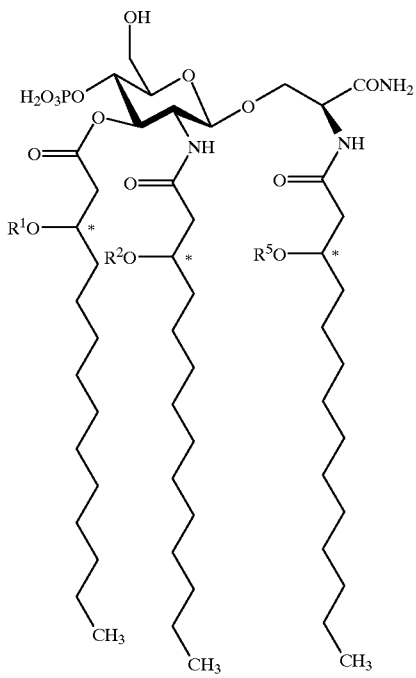

$R^1$, $R^2$ and $R^5$ = hexanoyl (stereochemistry* R, R, R)

Preferred embodiments of the invention are those compounds displaying low pyrogenicity and low potential to induce proinflammatory cytokines, regardless of activity on iNOS in monocytic cell lines.

Other compounds in the present invention exhibit suitable levels of activity in one or two of the assays described above.

| Compounds | $R^1$ | $R^2$ | $R^5$ | iNOS | pyrogenicity | cytokine stimulation |
|---|---|---|---|---|---|---|
| Disaccharides (compounds of formula IIa, above) | | | | | | |
| 5.07 | C14 | C14 | C14 | ++ | − | ++ |
| 5.11 | C10 | C10 | C10 | ++ | ++ | ++ |
| 5.28 | C14 | C12 | C16 | − | − | |
| 5.30 | C8 | C8 | C8 | ++ | ++ | − |
| 5.48 | C14 | C14 | C14 | | ++ | ++ |
| 5.49 | C14 | C14 | C14 | | ++ | ++ |
| 5.50 | C14 | C14 | C14 | ++ | ++ | ++ |
| 5.51 | C14 | C14 | C14 | | | ++ |
| 5.59 | C12 | C12 | C12 | | | ++ |
| 5.61 | C14 | ΔC12 | C16 | | | |
| Monosaccharides of the formula: | | | | | | |
| 5.26 | C6 | C6 | C6 | − | ++ | − |
| 5.54 | C7 | C7 | C7 | − | ++ | − |
| 5.66 | C6 | C10 | C10 | ++ | ++ | − |
| 5.67 | C6 | C6 | C10 | − | ++ | − |
| 5.68 | C6 | C10 | C6 | − | ++ | − |

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating diseases or conditions ameliorated by nitric oxide production in a subject comprising contacting said subject with an effective amount of a compound of the formula:

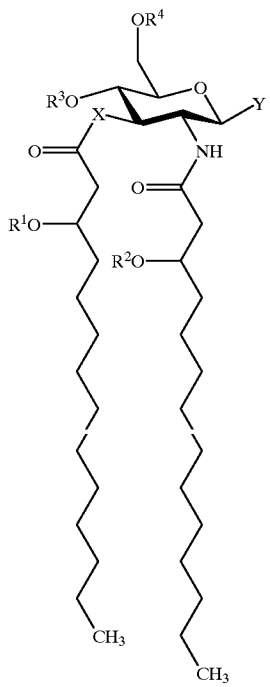

and

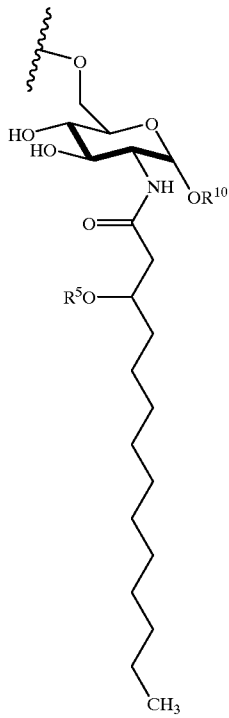

and pharmaceutically acceptable salts thereof, wherein

X is a member selected from the group consisting of —O— and —NH—;

$R^1$ and $R^2$ are each members independently selected from the group consisting of $(C_2–C_{24})$acyl;

$R^3$ is a member selected from the group consisting of —H and —PO$_3$R$^{11}$R$^{12}$, wherein $R^{11}$ and $R^{12}$ are each members independently selected from the group consisting of —H and $(C_1–C_4)$alkyl;

$R^4$ is a member selected from the group consisting of —H, —CH$_3$ and —PO$_3$R$^{13}$R$^{14}$, wherein $R^{13}$ and $R^{14}$ are each members independently selected from the group consisting of —H and $(C_1–C_4)$alkyl; and Y is a radical selected from the group consisting of

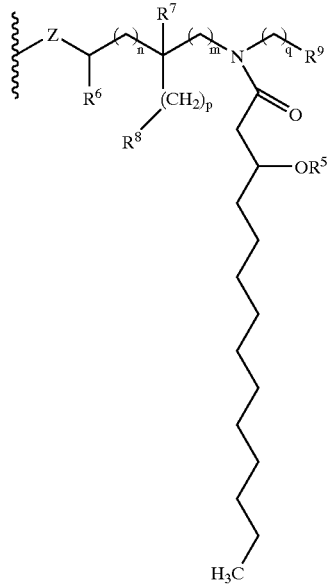

wherein the subscripts n, m, p and q are each independently an integer of from 0 to 6;

$R^5$ is $(C_2–C_{24})$acyl;

$R^6$ and $R^7$ are members independently selected from the group consisting of H and CH$_3$;

$R^8$ and $R^9$ are members independently selected from the group consisting of H, OH, $(C_1–C_4)$alkoxy, —PO$_3$H$_2$, —OPO$_3$H$_2$, —SO$_3$H, —OSO$_3$H, —NR$^{15}$R$^{16}$, —SR$^{15}$, —CN, —NO$_2$, —CHO, —CO$_2$R$^{15}$, and —CONR$^{15}$R$^{16}$, wherein $R^{15}$ and $R^{16}$ are each members independently selected from the group consisting of H and $(C_1–C_4)$alkyl;

$R^{10}$ is a member selected from the group consisting of H, CH$_3$, —PO$_3$H$_2$, ω-phosphonooxy$(C_2–C_{24})$alkyl, and ω-carboxy$(C_1–C_{24})$alkyl; and Z is —O— or —S—;

with the proviso that when $R^3$ is —PO$_3$R$^{11}$R$^{12}$, $R^4$ is other than —PO$_3$R$^{13}$R$^{14}$, and further proviso that when $R^3$ is —PO$_3$H$_2$, $R^4$ is H, $R^{10}$ is H, $R^1$ is n-tetradecanoyl, $R^2$ is n-octadecanoyl and $R^5$ is n-hexadecanoyl, then X is other than —O—, providing that the compound is other than monophosphoryl lipid A or 3-deacylated monophosphoryl lipid A.

2. A method in accordance with claim 1, wherein at least two of said $R^1$, $R^2$ and $R^5$ are selected from the group consisting of $(C_2-C_6)$acyl.

3. A method in accordance with claim 1, wherein two of said $R^1$, $R^2$ and $R^5$ are selected from the group consisting of $(C_2-C_6)$acyl and the total number of carbon atoms in $R^1$, $R^2$ and $R^5$ is from about 6 to about 22.

4. A method in accordance with claim 1, wherein two of said $R^1$, $R^2$ and $R^5$ are selected from the group consisting of $(C_2-C_6)$acyl and the total number of carbon atoms in $R^1$, $R^2$ and $R^5$ is from about 12 to about 18.

5. A method in accordance with claim 1, wherein X and Z are both —O—.

6. A method in accordance with claim 1, wherein $R^1$, $R^2$ and $R^5$ are each independently selected from the group consisting of $(C_{12}-C_{24})$acyl with the proviso that the total number of carbon atoms in $R^1$, $R^2$ and $R^5$ is from about 44 to about 60.

7. A method in accordance with claim 6, wherein said total number of carbon atoms is from about 46 to about 52.

8. A method in accordance with claim 6, wherein X and Z are both —O—.

9. A method in accordance with claim 1, wherein said compound is administered to said animal during the period from about 48 hours prior to the onset of ischemia, up to onset of ischemia.

10. A method in accordance with claim 1, wherein said compound is administered to said animal from immediately prior to the onset of ischemia through ischemia.

11. A method in accordance with claim 1, wherein said compound is administered to said animal from immediately prior to the onset of ischemia through reperfusion.

12. A method in accordance with claim 1, wherein said compound is administered to said animal parenterally or orally.

13. A method in accordance with claim 1, wherein said compound is administered to said animal intravenously.

14. A method in accordance with claim 1, wherein said compound is administered to said animal as a bolus.

15. A method in accordance with claim 1, wherein said compound is administered to said animal by infusion.

16. A method in accordance with claim 1, wherein said compound is administered to said animal intravenously as a bolus followed by infusion.

17. A method in accordance with claim 1, wherein said compound is administered to said animal for the treatment of ischemia followed by reperfusion which occurs during a medical procedure selected from the group consisting of surgery with major blood vessel cross-clamping, cardiac surgical procedures, organ transplants, tissue transplants, plastic surgery, myoplasty, skin flap translocation and bowel resection.

18. A method in accordance with claim 1, wherein said compound is administered to said animal for the treatment of ischemia followed by reperfusion which occurs during an event selected from the group consisting of myocardial infarction, stroke, drowning, bowel infarction and traumatic limb amputation and reattachment.

19. A method in accordance with claim 1, wherein said compound is administered to said animal for the treatment conditions involving the regulation of vascular tone, conditions arising from thrombotic (antiplatelet) events, pregnancy, coronary and peripheral artery disease, pulmonary diseases, bronchospasm, hypoxemia associated with thoracic surgery, or as an adjunct to thrombolysis to improve thrombolytic effect and reduce acute reclosure and protect tissue in the event of reclosure due to preconditioning effects, restenosis after PTCA or stenting, septic shock and multiple organ failure and to prevent thrombosis leading to MI or stroke.

20. A compound having the formula:

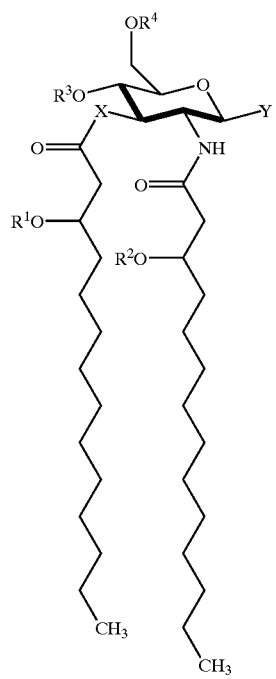

and pharmaceutically acceptable salts thereof, wherein

X is a member selected from the group consisting of —O— and —NH—;

$R^1$ and $R^2$ are each members independently selected from the group consisting of $(C_2-C_{24})$acyl;

$R^3$ is a member selected from the group consisting of —H and —$PO_3R^{11}R^{12}$, wherein $R^{11}$ and $R^{12}$ are each members independently selected from the group consisting of —H and $(C_1-C_4)$alkyl;

$R^4$ is a member selected from the group consisting of —H, —$CH_3$ and —$PO_3R^{13}R^{14}$, wherein $R^{13}$ and $R^{14}$ are each members independently selected from the group consisting of —H and $(C_1-C_4)$alkyl; and Y is a radical selected from the group consisting of

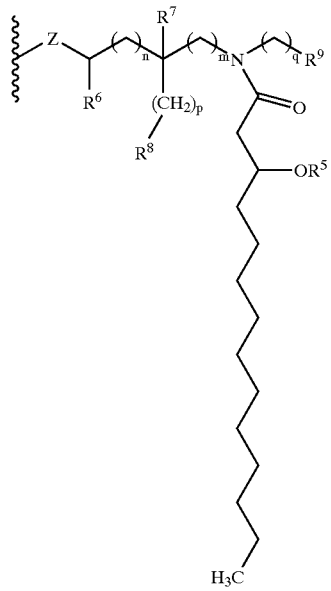

and

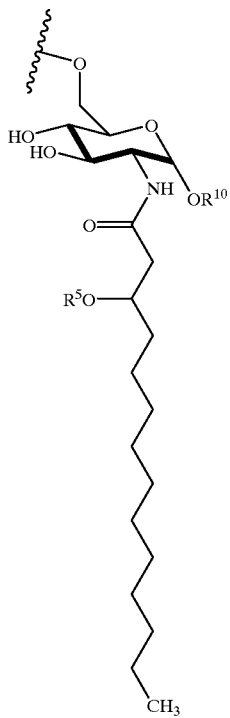

wherein the subscripts n, m, p and q are each independently an integer of from 0 to 6;
$R^5$ is $(C_2-C_{24})$acyl;
$R^6$ and $R^7$ are members independently selected from the group consisting of H and $CH_3$;
$R^8$ and $R^9$ are members independently selected from the group consisting of H, OH, $(C_1-C_4)$alkoxy, $-PO_3H_2$, $-OPO_3H_2$, $-SO_3H$, $-OSO_3H$, $-NR^{15}R^{16}$, $-SR^{15}$, $-CN$, $-NO_2$, $-CHO$, $-CO_2R^{15}$, and $-CONR^{15}R^{16}$, wherein $R^{15}$ and $R^{16}$ are each members independently selected from the group consisting of H and $(C_1-C_4)$alkyl;
$R^{10}$ is a member selected from the group consisting of H, $CH_3$, $-PO_3H_2$, ω-phosphonooxy$(C_2-C_{24})$alkyl, and ω-carboxy$(C_1-C_{24})$alkyl; and Z is $-O-$ or $-S-$;
with the proviso that
(a) when $R^3$ is $-PO_3R^{11}R^{12}$, $R^4$ is other than $-PO_3R^{13}R^{14}$, and with the further proviso that when $R^3$ is $-PO_3H_2$, $R^4$ is H, $R^{10}$ is H, $R^1$ is n-tetradecanoyl, $R^2$ is n-octadecanoyl and $R^5$ is n-hexadecanoyl, then X is other than $-O-$; and either
(b) at least two of $R^1$, $R^2$, and $R_5$ are $(C_2-C_6)$acly, or
(c) $R^1$, $R^2$ $R^5$ are each selected from $(C_{12}-C_{20})$acyl groups, wherein the total number of carbon atoms in $R^1$, $R^2$ and $R^5$ is from about 44 to about 60.

21. A compound of claim 20, wherein Y has the formula:

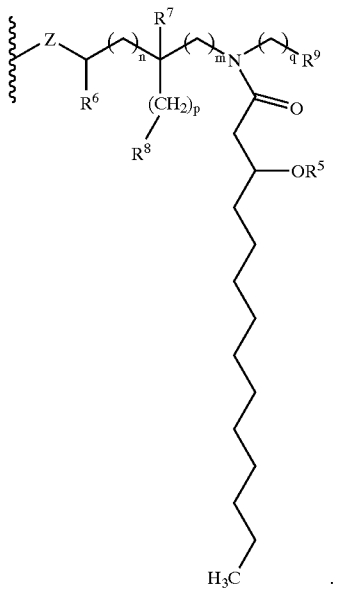

22. A compound of claim 20, wherein Y has the formula:

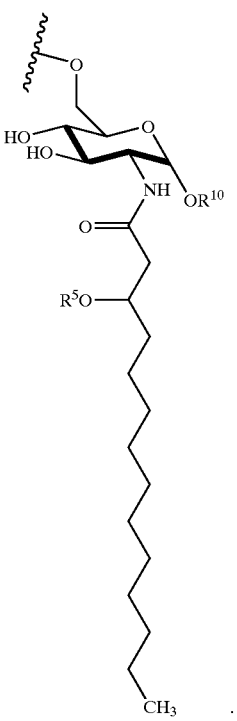

23. A compound of claim 22, wherein X is O; $R^1$, $R^2$ and $R^5$ are each acetyl, $R^3$ is —$PO_3H_2$ and $R^4$ is H.

24. A compound of claim 22, wherein X is O; $R^1$, $R^2$ and $R^5$ are each butyryl, $R^3$ is —$PO_3H_2$ and $R^4$ is H.

25. A compound of claim 22, wherein X is O; $R^1$, $R^2$ and $R^5$ are each hexanoyl, $R^3$ is —$PO_3H_2$ and $R^4$ is H.

26. A compound of claim 22, wherein X is O; $R^1$, $R^2$ and $R^5$ are each ($C_{14}$-$C_{18}$)acyl, $R^3$ is —$PO_3H_2$ and $R^4$ is H.

27. A compound in accordance with claim 20, wherein at least two of said $R^1$, $R^2$ and $R^5$ are selected from the group consisting of (C2–C6)acyl.

28. A compound in accordance with claim 20, wherein two of said $R^1$, $R^2$ and $R^5$ are selected from the group consisting of (C2–C6)acyl and the total number of carbon atoms in $R^1$, $R^2$ and $R^5$ is from about 6 to about 22.

29. A compound in accordance with claim 20, wherein two of said $R^1$, $R^2$ and $R^5$ are selected from the group consisting of (C2-C6)acyl and the total number of carbon atoms in $R^1$, $R^2$ and $R^5$ is from about 12 to about 18.

30. A compound in accordance with claim 20, wherein $R^1$, $R^2$ and $R^5$ are each independently selected from the group consisting of (C12–C24)acyl with the proviso that the total number of carbon atoms in $R^1$, $R^2$ and $R^5$ is from about 44 to about 60.

31. A compound in accordance with claim 30, wherein said total number of carbon atoms is from about 46 to about 52.

32. A pharmaceutical composition comprising a pharmaceutically acceptable carrier and a compound having the formula:

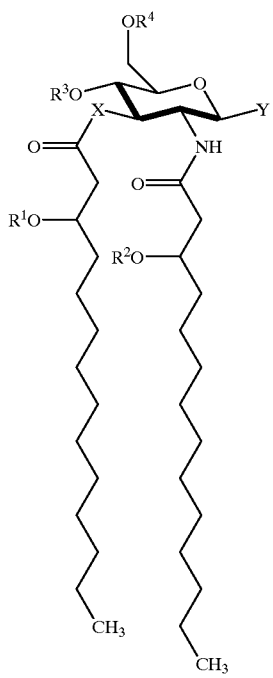

and pharmaceutically acceptable salts thereof, wherein
X is a member selected from the group consisting of —O— and —NH—;
$R^1$ and $R^2$ are each members independently selected from the group consisting Of ($C_2$–$C_{24}$)acyl;
$R^3$ is a member selected from the group consisting of —H and —$PO_3R^{11}R^{12}$, wherein $R^{11}$ and $R^{12}$ are each members independently selected from the group consisting of —H and ($C_1$–$C_4$)alkyl;
$R^4$ is a member selected from the group consisting of —H, —$CH_3$ and —$PO_3R^{13}R^{14}$, wherein $R^{13}$ and $R^{14}$ are each members independently selected from the group consisting of —H and ($C_1$–$C_4$)alkyl; and
Y is a radical selected from the group consisting of

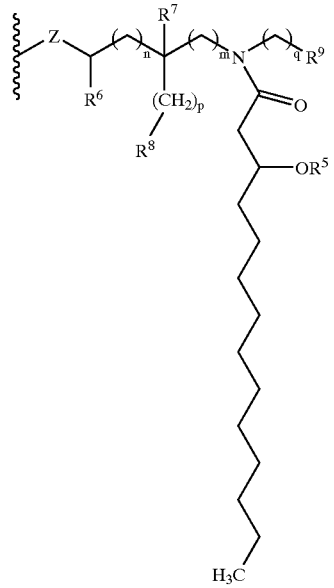

and

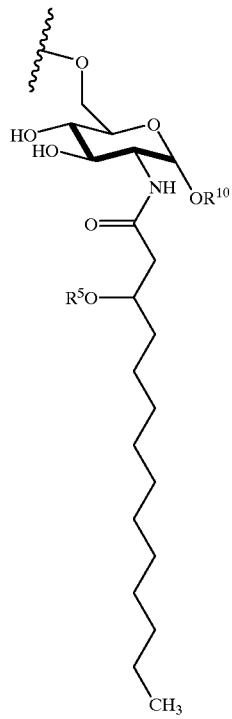

wherein the subscripts n, m, p and q are each independently an integer of from 0 to 6;
$R^5$ is ($C_2$–$C_{24}$)acyl;
$R^6$ and $R^7$ are members independently selected from the group consisting of H and $CH_3$;
$R^8$ and $R^9$ are members independently selected from the group consisting of H, OH, ($C_1C_4$)alkoxy, —$PO_3H_2$, —OPO$_3$H$_2$, —SO$_3$H, —OSO$_3$H, —NR$^{15}$R$^{16}$, —SR$^{15}$, —CN, —NO$_2$, —CHO, —CO$_2$R$^{15}$, and —CONR$^{15}$R$^{16}$, wherein R$^{15}$ and R$^{16}$ are each members independently selected from the group consisting of H and (C$_1$–C$_4$)alkyl;

R$^{10}$ is a member selected from the group consisting of H, CH$_3$, —PO$_3$H$_2$, ω-phosphonooxy(C$_2$–C$_{24}$)alkyl, and ω-carboxy(C$_1$–C$_{24}$)alkyl; and Z is —O— or —S—;

with the proviso that (a) when R$^3$ is —PO$_3$R$^{11}$R$^{12}$, R$^4$ is other than —PO$_3$R$^{13}$R$^{14}$, and with the further proviso that when R$^3$ is —PO$_3$H$_2$, R$^4$ is H, R$^{10}$ is H, R$^1$ is n-tetradecanoyl, R$^2$ is n-octadecanoyl and R$^5$ is n-hexadecanoyl, then X is other than —O—; and either (b) at least two of R$^1$, R$^2$, and R$^5$ (C$_2$–C$_6$)acyl, or (c) R$^1$, R$^2$ and R$^5$ are each selected from (C$_2$–C$_{20}$)acyl groups, wherein the total number of carbon atoms in R$^1$, R$^2$ and R$^5$ is from about 44 to about 60 and further providing that the compound is other than monophosphoryl lipid A or 3-deacylated monophosphoryl lipid A.

33. A composition in accordance with claim 32, wherein said pharmaceutically acceptable carrier is selected from the group consisting of water for injection, polyethylene glycol, propylene glycol and ethanol, oil-in-water emulsions, liposomes, lipid vesicles and surfactant containing vesicles.

34. A method of inducing inducible nitric oxide synthase or activation of constitutive nitric oxide synthase in a tissue selective or specific manner, comprising administering to an animal capable of producing or activating nitric oxide synthase an effective amount of a compound having the formula:

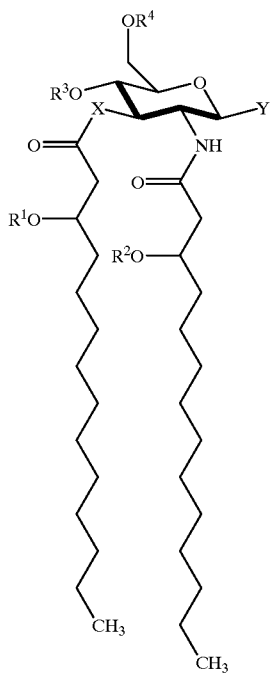

and pharmaceutically acceptable salts thereof, wherein

X is a member selected from the group consisting of —O— and —NH—; R$^1$ and R$^2$ are each members independently selected from the group consisting of (C$_2$–C$_{24}$)acyl;

R$^3$ is a member selected from the group consisting of —H and —PO$_3$R$^{11}$R$^{12}$, wherein R$^{11}$ and R$^{12}$ are each members independently selected from the group consisting of —H and (C$_1$–C$_4$)alkyl;

R$^4$ is a member selected from the group consisting of —H, —CH$_3$ and —PO$_3$R$^{13}$R$^{14}$, wherein R$^{13}$ and R$^{14}$ are each members independently selected from the group consisting of —H and (C$_1$–C$_4$)alkyl; and Y is a radical selected from the group consisting of

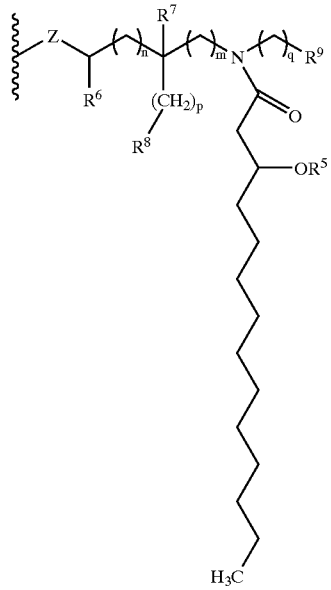

and

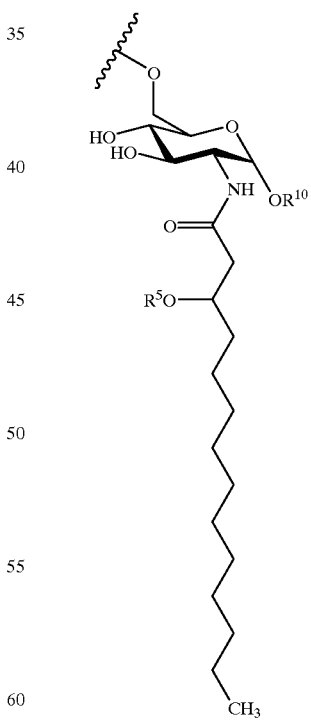

wherein the subscripts n, m, p and q are each independently an integer of from 0 to 6;

R$^5$ is (C$_2$–C$_{24}$)acyl;

R$^6$ and R$^7$ are members independently selected from the group consisting of H and CH$_3$;

$R^8$ and $R^9$ are members independently selected from the group consisting of H, OH, $(C_1C_4)$alkoxy, —$PO_3H_2$, —$OPO_3H_2$, —$SO_3H$, —$OSO_3H$, —$NR^{15}R^{16}$, —$SR^{15}$, —CN, —$NO_2$, —CHO, —$CO_2R^{15}$, and —$CONR^{15}R^{16}$, wherein $R^{15}$ and $R^{16}$ are each members independently selected from the group consisting of H and $(C_1-C_4)$alkyl;

$R^{10}$ is a member selected from the group consisting of H, $CH_3$, —$PO_3H_2$, ω-phosphonooxy$(C_2-C_{24})$alkyl, and ω-carboxy$(C_1-C_{24})$alkyl; and Z is —O— or —S—;

with the proviso that (a) when $R^3$ is —$PO_3R^{11}R^{12}$, $R^4$ is other than —$PO_3R^{13}R^{14}$, and with the further proviso that when $R^3$ is —$PO_3H_2$, $R^4$ is H, $R^{10}$ is H, $R^1$ is n-tetradecanoyl, $R^2$ is n-octadecanoyl and $R^5$ is n-hexadecanoyl, then X is other than —O—; and either (b) at least two of $R^1$, $R^2$, and $R^5$ are $(C_2-C_6)$acyl, or (c) $R^1$, $R^2$ and $R^5$ are each selected from $(C_{12}-C_{20})$acyl groups, wherein the total number of carbon atoms in $R^1$, $R^2$ and $R^5$ is from about 44 to about 60 and further providing that the compound is other than monophosphoryl lipid A or 3-deacylated monophosphoryl lipid A.

35. A method of inducing inducible nitric oxide synthase or activation of constitutive nitric oxide synthase in a tissue selective or specific manner with low potential for pyrogenicity or ability to induce proinflammatory cytokines, comprising administering to an animal capable of producing or activating nitric oxide synthase an effective amount of a compound having the formula:

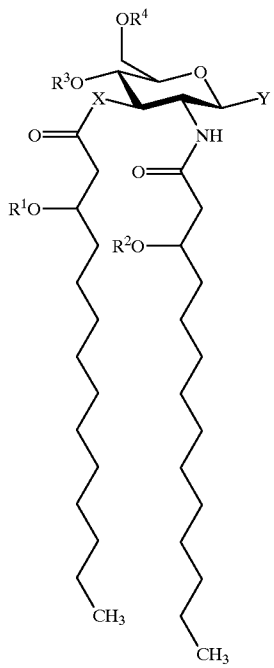

and pharmaceutically acceptable salts thereof, wherein

X is a member selected from the group consisting of —O— and —NH—;

$R^1$ and $R^2$ are each members independently selected from the group consisting of $(C_2-C_{24})$acyl;

$R^3$ is a member selected from the group consisting of —H and —$PO_3R^{11}R^{12}$, wherein $R^{11}$ and $R^{12}$ are each members independently selected from the group consisting of —H and $(C_1-C_4)$alkyl;

$R^4$ is a member selected from the group consisting of —H, —$CH_3$ and —$PO_3R^{13}R^{14}$, wherein $R^{13}$ and $R^{14}$ are each members independently selected from the group consisting of —H and $(C_1-C_4)$alkyl; and Y is a radical selected from the group consisting of

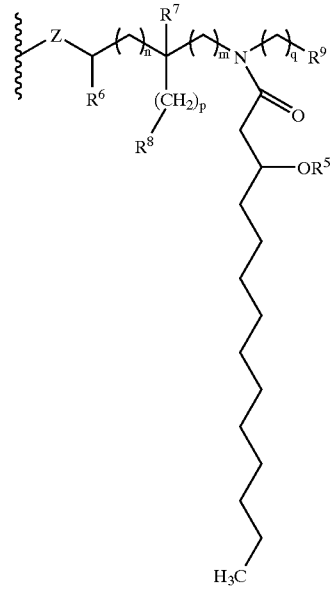

and

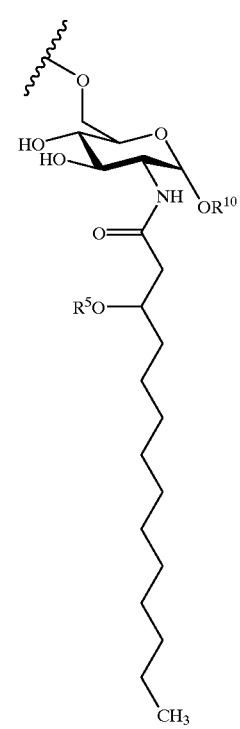

wherein the subscripts n, m, p and q are each independently an integer of from 0 to 6;

$R^5$ is $(C_2-C_{24})$acyl;

$R^6$ and $R^7$ are members independently selected from the group consisting of H and $CH_3$;

$R^8$ and $R^9$ are members independently selected from the group consisting of H, OH, $(C_1C_4)$alkoxy, —$PO_3H_2$, —OPO$_3$H$_2$, —SO$_3$H, —OSO$_3$H, —NR$^{15}$R$^{16}$, —SR$^{15}$, —CN, —NO$_2$, —CHO, —CO$_2$R$^{15}$, and —CONR$^{15}$R$^{16}$, wherein R$^{15}$ and R$^{16}$ are each members independently selected from the group consisting of H and (C$_1$–C$_4$)alkyl;

R$^{10}$ is a member selected from the group consisting of H, CH$_3$, —PO$_3$H$_2$, ω-phosphonooxy(C$_2$–C$_{24}$)alkyl, and ω-carboxy(C$_1$–C$_{24}$)alkyl; and Z is —O— or —S—;

with the proviso that (a) when R$^3$ is —PO$_3$R$^{11}$R$^{12}$, R$^4$ is other than —PO$_3$R$^{13}$R$^{14}$, and with the further proviso that when R$^3$ is —PO$_3$H$_2$, R$^4$ is H, R$^{10}$ is H, R$^{11}$ is n-tetradecanoyl, R$^2$ is n-octadecanoyl and R$^5$ is n-hexadecanoyl, then X is other than —O—; and either (b) at least two of R$^1$, R$^2$, and R$^5$ are (C$_2$–C$_6$)acyl, or (c) R$^1$, R$^2$ and R$^5$ are each selected from (C$_{12}$–C$_{20}$)acyl groups, wherein the total number of carbon atoms in R$^1$, R$^2$ and R$^5$ is from about 44 to about 60 and further providing that the compound is other than monophosphoryl lipid A or 3-deacylated monophosphoryl lipid A.

* * * * *